(12) United States Patent
Namba et al.

(10) Patent No.: US 8,370,084 B2
(45) Date of Patent: Feb. 5, 2013

(54) METHOD FOR ESTIMATING PHYSICAL PROPERTY OF CERAMIC, METHOD FOR ESTIMATING PHYSICAL PROPERTY OF THERMAL BARRIER COATING, METHOD FOR ESTIMATING REMAINING LIFETIME OF THERMAL BARRIER COATING, METHOD FOR ESTIMATING REMAINING LIFETIME OF HIGH-TEMPERATURE MEMBER, AND PHYSICAL PROPERTY ACQUIRING APPARATUS

(75) Inventors: Katsumi Namba, Hyogo (JP); Taiji Torigoe, Hyogo (JP); Ikuo Okada, Hyogo (JP); Kazutaka Mori, Hyogo (JP); Yasuhiko Tsuru, Hyogo (JP); Masato Shida, Hyogo (JP); Ichiro Nagano, Hyogo (JP); Eisaku Ito, Hyogo (JP); Koji Takahashi, Hyogo (JP)

(73) Assignee: Mitsubishi Heavy Industries, Ltd., Tokyo (JP)

( * ) Notice: Subject to any disclaimer, the term of this patent is extended or adjusted under 35 U.S.C. 154(b) by 106 days.

(21) Appl. No.: 12/681,704
(22) PCT Filed: Mar. 13, 2009
(86) PCT No.: PCT/JP2009/054893
§ 371 (c)(1),
(2), (4) Date: Apr. 5, 2010
(87) PCT Pub. No.: WO2009/119344
PCT Pub. Date: Oct. 1, 2009

(65) Prior Publication Data
US 2010/0217540 A1    Aug. 26, 2010

(30) Foreign Application Priority Data
Mar. 26, 2008  (JP) ................................. 2008-081848

(51) Int. Cl.
*G01B 3/44*    (2006.01)
*C22C 32/00*   (2006.01)
*B05D 3/02*    (2006.01)

(52) U.S. Cl. .............................. 702/34; 419/19; 427/559
(58) Field of Classification Search ............. 702/34–36, 702/42–43, 81, 84, 127–128, 130–132, 134, 702/136, 155–157, 166, 170, 172, 182–184, 702/189; 419/2, 19–22, 35; 427/446, 455–456, 427/557, 559, 576; 428/357, 361, 403, 621, 428/628–630, 632–633
See application file for complete search history.

(56) References Cited

U.S. PATENT DOCUMENTS
2002/0013643 A1    1/2002  Ishii et al.

FOREIGN PATENT DOCUMENTS
EP    1852697 A    11/2007
JP    63-117962 A    5/1988
(Continued)

OTHER PUBLICATIONS
Fujii et al., Development of Operating Temperature Prediction Method Using Thermophysical Properties Change of Thermal Barrier Coatings, Jan. 2004, Transactions of the ASME, vol. 126, pp. 102-106.*

(Continued)

*Primary Examiner* — Toan Le
(74) *Attorney, Agent, or Firm* — Westerman, Hattori, Daniels & Adrian, LLP

(57) ABSTRACT

A method by which physical properties, including the Young's modulus and thermal conductivity of a ceramic layer of a thermal barrier coating formed on a high-temperature member, are quickly and accurately estimated. A method for estimating a physical property of a ceramic includes a step of calculating the Larson-Miller parameter from the time for which and the temperature at which the ceramic is heated; a step of acquiring the porosity of the ceramic corresponding to the calculated Larson-Miller parameter, based on the calculated Larson-Miller parameter and a diagram correlating the Larson-Miller parameter and the porosity obtained from samples having the same composition as the ceramic; and a step of acquiring the physical property of the ceramic corresponding to the acquired porosity, based on the acquired porosity and a diagram correlating the porosity and the physical property obtained from samples having the same composition as the ceramic.

14 Claims, 3 Drawing Sheets

FOREIGN PATENT DOCUMENTS

| | | |
|---|---|---|
| JP | 8-254530 A | 10/1996 |
| JP | 11-236268 A | 8/1999 |
| JP | 2003-4549 A | 1/2003 |
| JP | 2003-074376 A | 3/2003 |
| JP | 2008-14748 A | 1/2008 |

OTHER PUBLICATIONS

Zhu et al., Thermal Conductivity and Elastic Modulus Evolution of Thermal Barrier Coatings Under High Heat Flux Conditions, Apr. 1999, NASA/TM-1999-209069, 21 pp.*

International Search Report of PCT/JP2009/054893, Mailing Date of May 26, 2009.

Extended European Search Report dated Sep. 14, 2012, issued in corresponding European Patent Application No. 09726297.6, (6 pages).

Zhu, et al., "Thermal Conductivity and Elastic Modulus Evolution of Thermal Barrier Coatings under High Heat Flux Conditions", Journal of Thermal Spray Technology, dated Jun. 1, 2000, vol. 9, No. 2, (pp. 175-180), XP008150517. Cited in Extended European Search Report dated Sep. 14, 2012.

* cited by examiner

METHOD FOR ESTIMATING PHYSICAL PROPERTY OF CERAMIC, METHOD FOR ESTIMATING PHYSICAL PROPERTY OF THERMAL BARRIER COATING, METHOD FOR ESTIMATING REMAINING LIFETIME OF THERMAL BARRIER COATING, METHOD FOR ESTIMATING REMAINING LIFETIME OF HIGH-TEMPERATURE MEMBER, AND PHYSICAL PROPERTY ACQUIRING APPARATUS

TECHNICAL FIELD

The present invention relates to a method for estimating a physical property of a ceramic, a method for estimating a physical property of a thermal barrier coating, a method for estimating the remaining lifetime of a thermal barrier coating, a method for estimating the remaining lifetime of a high-temperature member, and a physical property acquiring apparatus, and particularly to a method for estimating a physical property of a thermal barrier coating formed on a high-temperature member.

BACKGROUND ART

High-temperature members for use in high-temperature environments, such as moving blades, stationary blades, and combustors of gas turbines for power generation and jet engines, have thermal barrier coatings (TBCs) applied to their substrate surfaces in order to protect substrates made from metals from high temperatures. Thermal barrier coatings are composed of a metal junction layer formed on the substrate by low-pressure plasma spraying or the like and a ceramic layer formed on the metal junction layer by atmospheric plasma spraying. Materials including rare earth stabilized zirconias such as yttria-stabilized zirconia (YSZ) are used for the ceramic layer.

If damage, such as fracture or exfoliation, to the ceramic layer of a thermal barrier coating occurs during operation of a machine component such as a turbine or a jet engine, the temperature of the metal substrate of the high-temperature member rises, leading to breakage of the machine component. Therefore, it is necessary to determine the durability and remaining lifetime of the ceramic layer of the thermal barrier coating before or during operation of the machine component. To determine the durability and lifetime of a thermal barrier coating, a high-temperature member can be heated at use temperature for the use time; however, this is not realistic because a prolonged period of time is required to obtain test results. For this reason, a process of obtaining long-term test results by extrapolating from short-term test results using the Larson-Miller parameter is performed.

Patent Citation 1 discloses a method for estimating the temperature of a ceramic layer as a physical property that is useful for a durability assessment or a remaining lifetime assessment of a ceramic layer. Specifically, the surface temperature of the ceramic layer is estimated by substituting into a characteristic diagram showing the relationship between the area ratio of gap-like defects (stratified formation defects) and the value of the Larson-Miller parameter, obtained using a sample having the same composition as the ceramic layer, a measured value of the area ratio of gap-like defects in a cross section of a ceramic layer in a depth direction when the real machine has been used for a predetermined period of time.

Patent Citation 1: Japanese Unexamined Patent Application, Publication No. 2003-4549

DISCLOSURE OF INVENTION

A ceramic layer of a thermal barrier coating has a large number of stratified formation defects and pores inside. When a high-temperature member is used under a high-temperature environment for a long period of time, sintering of the thermal barrier coating proceeds, and the sizes of the inside stratified formation defects and pores decrease. In response to the change of the stratified formation defects and pores, the Young's modulus and thermal conductivity of the ceramic layer also change.

Like the surface temperature of the above-described ceramic layer, the Young's modulus and thermal conductivity of a ceramic layer are physical properties that influence the durability and remaining lifetime of the ceramic layer. Thus, these physical properties also need to be controlled before or during operation of a machine component.

Conventionally, with respect to each operating condition of a real turbine, it is necessary to prepare a test piece and measure the Young's modulus and the thermal conductivity, and enormous amounts of cost and time are required to produce test pieces and measure the physical properties. Accordingly, there is a need for a method for estimating a physical property of a ceramic layer of a thermal barrier coating with high accuracy in a simpler and quicker manner and, furthermore, estimating the remaining lifetime of the thermal barrier coating, before and during operation of a turbine.

The present invention provides a method by which physical properties, in particular, the Young's modulus and thermal conductivity of a ceramic layer of a thermal barrier coating formed on a high-temperature member are accurately estimated in a short period of time.

To solve the above-described problems, the present invention provides a method for estimating a physical property of a ceramic, the method including a step of calculating a Larson-Miller parameter from a time for which and a temperature at which the ceramic is heated; a step of acquiring a porosity of the ceramic corresponding to the calculated Larson-Miller parameter, based on the calculated Larson-Miller parameter and a diagram correlating the Larson-Miller parameter and the porosity obtained from samples having the same composition as the ceramic; and a step of acquiring the physical property of the ceramic corresponding to the acquired porosity, based on the acquired porosity and a diagram correlating the porosity and the physical property obtained from samples having the same composition as the ceramic.

According to the present invention, a diagram correlating the Larson-Miller parameter and the porosity and a diagram correlating the porosity and the physical property are created beforehand from samples having the same composition as the ceramic whose physical property is to be estimated. The Larson-Miller parameter is calculated from the time for which and the temperature at which the ceramic whose physical property is to be estimated is heated. The porosity corresponding to the calculated Larson-Miller parameter is acquired based on the calculated Larson-Miller parameter and the previously created diagram correlating the Larson-Miller parameter and the porosity. The acquired porosity is taken as an estimated value of the porosity of the ceramic. Then, the physical property corresponding to the acquired porosity is acquired based on the acquired porosity and the previously created diagram correlating the porosity and the physical property. The acquired physical property is taken as an estimated value of the physical property of the ceramic.

As a result of expressing the time for which and the temperature at which the ceramic is heated as the Larson-Miller parameter, a correlation diagram obtained from short-time test results can also be applied to estimation of a physical property of the ceramic when the ceramic has been heated for a long period of time. Moreover, as a result of using the diagram correlating the porosity and the physical property, the acquired physical property is accurate. Therefore, the use of the above-described correlation diagrams makes it possible to estimate the physical property of the ceramic with high accuracy in a short period of time.

In the above-described invention, it is preferable that the physical property is Young's modulus. Young's modulus has a strong correlation with pores and stratified formation defects inside a ceramic. With the present invention, the Young's modulus of a ceramic heat-treated under conditions of high temperature and long duration can be accurately estimated in a short period of time.

In the above-described invention, it is preferable that the physical property is thermal conductivity. Thermal conductivity has a strong correlation with pores and stratified formation defects inside a ceramic. With the present invention, the thermal conductivity of a ceramic heat-treated under conditions of high temperature and long duration can be estimated with high accuracy in a short period of time.

The present invention provides a method for estimating a physical property of a thermal barrier coating, wherein at least one of the Young's modulus and the thermal conductivity of a ceramic layer of the thermal barrier coating formed on a high-temperature member is acquired using the above-described method for estimating a physical property of a ceramic.

For example, if the above-described correlation diagrams are created beforehand based on the results obtained during the development stage of the material for the ceramic layer of the thermal barrier coating, those correlation diagrams can also be applied to a real machine. Therefore, before or during operation of the real machine, the physical property of the ceramic layer of the thermal barrier coating can be estimated in a short period of time from the operating conditions. Moreover, since the Young's modulus or the thermal conductivity of the ceramic layer is obtained using the diagram correlating the Young's modulus or the thermal conductivity and the porosity, which has a very strong correlation with the Young's modulus or the thermal conductivity, the Young's modulus or the thermal conductivity can be estimated with high accuracy. Thus, the time and cost required for acquiring the physical property of the thermal barrier coating can be significantly reduced, and the accuracy with which the physical property of the thermal barrier coating is estimated can be improved.

The present invention provides a method for estimating a remaining lifetime of a thermal barrier coating, wherein the remaining lifetime of the thermal barrier coating is acquired using at least one of the Young's modulus and the thermal conductivity of the ceramic layer acquired by using the above-described method for estimating a physical property of a thermal barrier coating. Moreover, the present invention provides a method for estimating a remaining lifetime of a high-temperature member, wherein the remaining lifetime of the high-temperature member is estimated from the remaining lifetime of the thermal barrier coating acquired by using the above-described method for estimating a remaining lifetime of a thermal barrier coating.

With the above-described method for estimating a physical property of a ceramic, the Young's modulus and the thermal conductivity of the ceramic layer of the thermal barrier coating can be acquired accurately. Accordingly, the value of the remaining lifetime of the thermal barrier coating acquired by using at least one of the acquired Young's modulus and thermal conductivity of the thermal barrier coating, and the value of the remaining lifetime of the high-temperature member acquired from the remaining lifetime of the thermal barrier coating are also accurate. Thus, in the case of, for example, a turbine, if the remaining lifetimes of the thermal barrier coating and the high-temperature member are estimated beforehand using the present invention before or during operation of the turbine, a maintenance check of the high-temperature member can be performed before the thermal barrier coating is damaged. Consequently, an emergency shutdown due to breakage of the high-temperature member is avoided, and thus, an economic loss can be prevented.

The present invention provides a physical property acquiring apparatus including a Larson-Miller parameter calculating section for calculating a Larson-Miller parameter from a time for which and a temperature at which a ceramic is heated; a porosity acquiring section for acquiring a porosity of the ceramic corresponding to the calculated Larson-Miller parameter, based on the Larson-Miller parameter calculated by the calculating section and a diagram correlating the Larson-Miller parameter and the porosity obtained from samples having the same composition as the ceramic; and a physical property acquiring section for acquiring a physical property of the ceramic corresponding to the acquired porosity, based on the porosity acquired by the porosity acquiring section and a diagram correlating the porosity and the physical property obtained from samples having the same composition as the ceramic.

With the above-described apparatus for acquiring a physical property, a physical property of a ceramic to be heat-treated under conditions of high temperature and long duration can be acquired and estimated quickly with high accuracy before heating.

In the above-described invention, it is preferable that the physical property acquiring apparatus further includes a remaining lifetime acquiring section for acquiring a remaining lifetime of a thermal barrier coating using the physical property acquired by the physical property acquiring section. The remaining lifetime of the thermal barrier coating can thus be acquired in a shorter period of time.

According to the present invention, a physical property of a ceramic, especially a ceramic layer of a thermal barrier coating can be accurately estimated in a short period of time. Thus, the cost and time required for acquiring the physical property can be significantly reduced.

Moreover, according to the present invention, the remaining lifetime of a thermal barrier coating and the remaining lifetime of a high-temperature member provided with the thermal barrier coating can be estimated with high accuracy in a short period of time. Thus, in the case of, for example, a turbine, if the remaining lifetimes of the thermal barrier coating and the high-temperature member are estimated beforehand using the present invention before or during operation of the turbine, a maintenance check of the high-temperature member can be performed before the thermal barrier coating is damaged. Consequently, an emergency shutdown due to breakage of the high-temperature member is avoided, and thus, an economic loss can be prevented.

BEST MODE FOR CARRYING OUT THE INVENTION

Hereinafter, an embodiment of a physical property acquiring apparatus and a method for estimating a physical property of a ceramic according to the present invention will be described. In the present embodiment, a ceramic layer of a thermal barrier coating formed on a high-temperature member of a turbine is taken as an example of the ceramic.

In the present embodiment, a computer serves as a physical property acquiring apparatus.

First, an operator creates a graph showing the correlation between the Larson-Miller parameter and the porosity.

The operator produces a plurality of samples having a ceramic coating formed by thermally spraying ceramic powders having the same composition as the ceramic layer of the thermal barrier coating onto a metal substrate made from the same material as the turbine. The operator heats each of the samples under different heating conditions (heating temperature and heating time) using an electric furnace.

The operator observes the cross-sectional microstructure of the substrate under test before and after heating using a microscope. An optical microscope or a scanning electron microscope can be used as the microscope.

Figure 1:
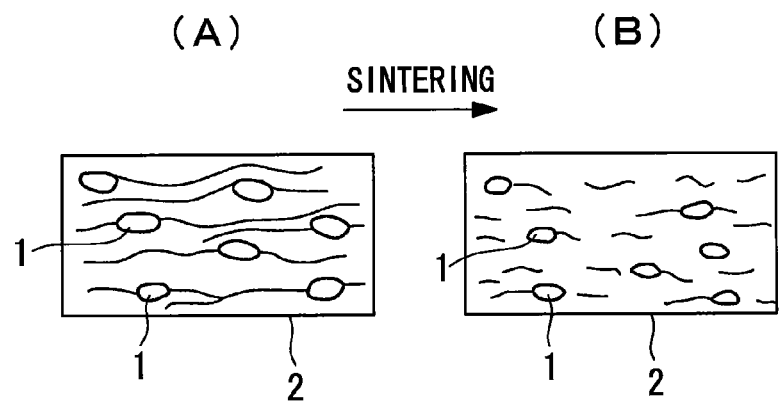
FIG. 1 A diagram schematically showing the cross-sectional microstructure of a thermal barrier coating before (A) and after (B) heating.

FIG. 1 is a diagram schematically showing the cross-sectional microstructure of the thermal barrier coating before (A) and after (B) heating. In the cross-sectional microstructure of the thermal barrier coating before heating, pores 1 and stratified formation defects 2 are present as shown in FIG. 1(A). When the thermal barrier coating is heated at a high temperature, the cross-sectional microstructure changes as shown in FIG. 1(B). That is to say, as sintering proceeds, the sizes of the pores 1 and the stratified formation defects 2 decrease, and their numbers also decrease.

The operator performs image processing on the micrographs to create binary images. Pores and stratified formation defects in the created binary images are detected. The area of the detected pores and stratified formation defects is measured, and the porosity and the area ratio of the stratified formation defects are calculated. The calculated area ratio is used as the porosity of the samples.

The operator calculates the Larson-Miller parameter from the temperature at which and the time for which the samples are heated. The Larson-Miller parameter LMP is expressed by the following formula (1):

$$LMP = T(20 + \log t)/1000 \quad (1)$$

where T is the heating temperature, and t is the heating time.

It should be noted that the Larson-Miller parameter of the above-described samples may also be calculated by the physical property acquiring apparatus. In this case, the operator inputs the temperature at which and the time for which the samples are heated to the physical property acquiring apparatus. A Larson-Miller parameter calculating section of the physical property acquiring apparatus calculates the Larson-Miller parameter of the samples from the input heating time and heating temperature using the formula (1).

The operator creates a graph representing the correlation between the calculated Larson-Miller parameter of the samples and the porosity of the samples (hereinafter referred to as correlation diagram A).

Figure 2:
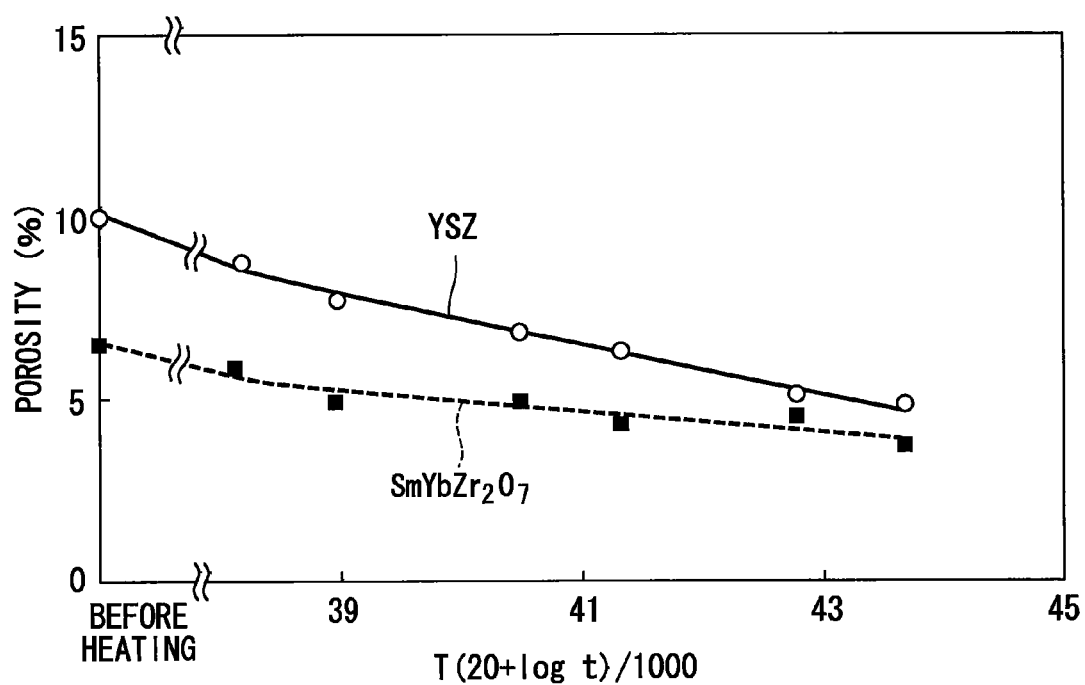
FIG. 2 An example of a diagram A correlating the Larson-Miller parameter and the porosity.

FIG. 2 shows an example of a correlation diagram A for samples having an yttria-stabilized zirconia (YSZ) coating and samples having an $SmYbZr_2O_7$ coating formed thereon. In this figure, the horizontal axis is the Larson-Miller parameter, and the vertical axis is porosity. The porosity was determined based on backscattered electron images (BSEs) obtained by scanning electron microscope observation. As shown in FIG. 2, the relationship between the Larson-Miller parameter and the porosity is different between YSZ and $SmYbZr_2O_7$. Therefore, the operator creates a different correlation diagram A for each material.

The operator inputs the created correlation diagram A to a physical property acquiring apparatus. The physical property acquiring apparatus stores the input correlation diagram A into a memory of a computer.

Next, the operator creates a graph representing the correlation between the porosity and a physical property.

The operator measures a physical property of the above-described samples. Physical properties measured in the present embodiment are Young's modulus and thermal conductivity.

The operator cuts test pieces for physical property measurement having the shape and size defined by the JIS standard, from the samples before and after heating. The operator measures the Young's modulus and thermal conductivity using the cut test pieces.

The operator creates a graph representing the correlation between the porosity of the samples and the Young's modulus of the test pieces (hereinafter referred to as correlation diagram B). The operator creates a graph representing the correlation between the porosity of the samples and the thermal conductivity of the test pieces (hereinafter referred to as correlation diagram C).

Figure 3:
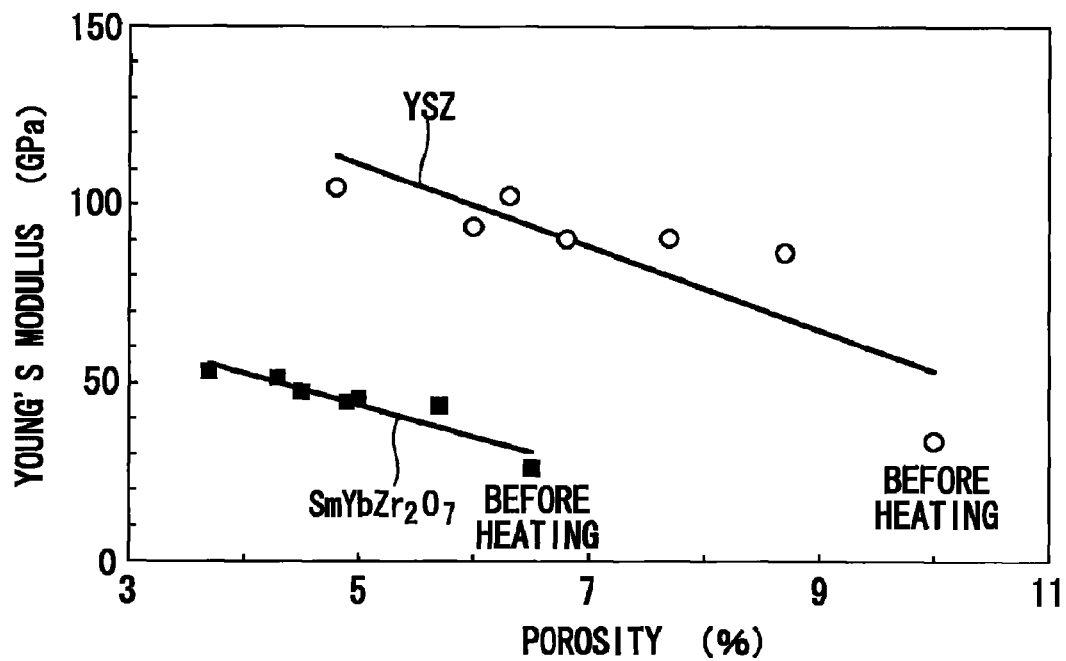
FIG. 3 An example of a diagram B correlating the porosity and the Young's modulus.
Figure 4:
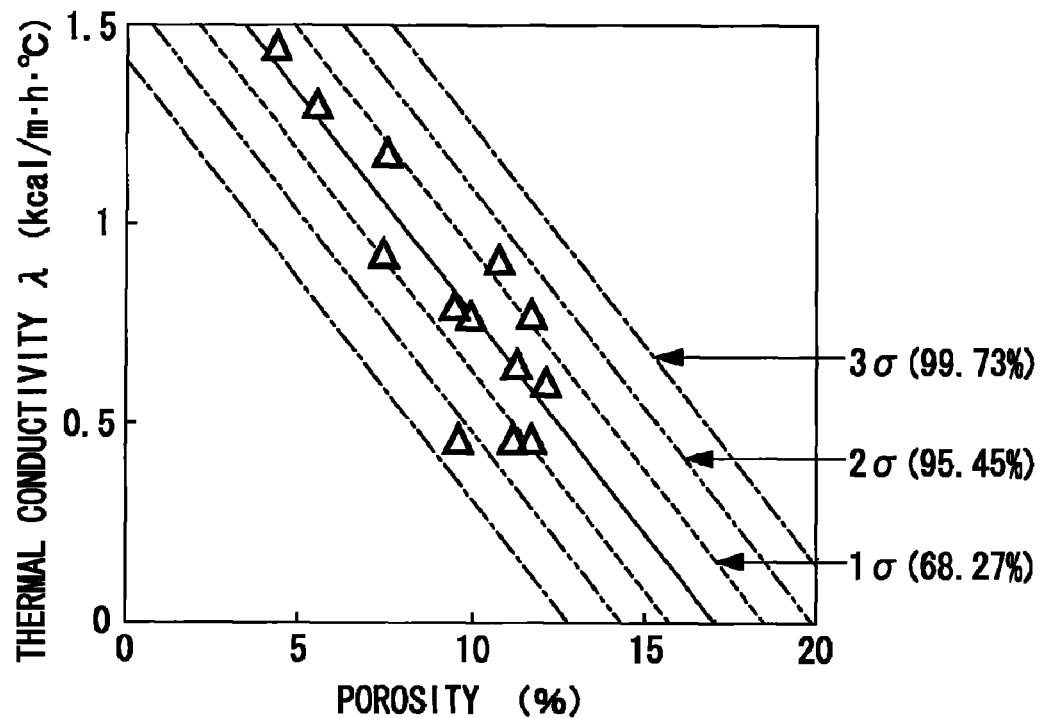
FIG. 4 An example of a diagram C correlating the porosity and the thermal conductivity in the case where backscattered electron images from a scanning electron microscope are used.

FIG. 3 shows an example of a correlation diagram B for the samples having the YSZ coating and the samples having the $SmYbZr_2O_7$ coating formed thereon, where the horizontal axis is porosity and the vertical axis is Young's modulus. FIG. 4 shows an example of a correlation diagram C for the samples having the YSZ coating and the samples having the $SmYbZr_2O_7$ coating formed thereon, where the horizontal axis is porosity and the vertical axis is thermal conductivity. It should be noted that FIGS. 3 and 4 were obtained from the porosity determined based on the backscattered electron images (BSEs) obtained by scanning electron microscope observation. As can be seen from these figures, the correlation between the porosity and each physical property is different between YSZ and $SmYbZr_2O_7$. Therefore, the operator creates a correlation diagram B and a correlation diagram C for each material.

The operator inputs the created correlation diagrams B and C to the physical property acquiring apparatus. The physical property acquiring apparatus stores the input correlation diagrams B and C into the memory of the computer.

The physical property acquiring apparatus of the present embodiment acquires a physical property of the ceramic layer of the thermal barrier coating formed on the turbine member, using the correlation diagrams A to C stored in the memory of the computer.

The operator inputs, as the operating conditions of the turbine, the operating temperature and the operating time to the physical property acquiring apparatus. The Larson-Miller parameter calculating section of the physical property acquiring apparatus calculates the Larson-Miller parameter from the input operating temperature and operating time.

A porosity acquiring section of the physical property acquiring apparatus calls up the correlation diagram A from the memory. The porosity acquiring section of the physical property acquiring apparatus acquires the value of porosity corresponding to the calculated Larson-Miller parameter described above, based on the called correlation diagram A.

A physical property acquiring section of the physical property acquiring apparatus calls up the correlation diagram B from the memory. The physical property acquiring section of the physical property acquiring apparatus acquires the value of Young's modulus corresponding to the acquired value of porosity described above, based on the called correlation diagram B.

The physical property acquiring section of the physical property acquiring apparatus calls up the correlation diagram C from the memory. The physical property acquiring section of the physical property acquiring apparatus acquires the value of thermal conductivity corresponding to the acquired value of porosity described above, based on the called correlation diagram C.

The operator estimates that the values of Young's modulus and thermal conductivity acquired by the physical property acquiring apparatus are the Young's modulus and the thermal conductivity of the ceramic layer when the turbine has been operated under the above-described operating conditions.

In the above-described embodiment, the backscattered electron images from the scanning electron microscope are used to detect the pores and stratified formation defects; however, an optical microscope image or a secondary electron image from a scanning electron microscope can also be used.

Figure 5:
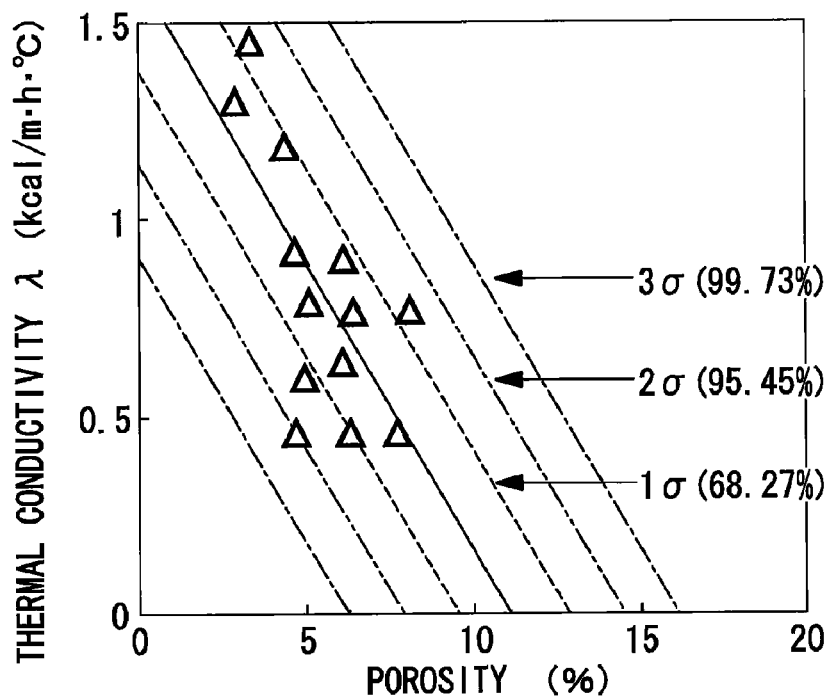
FIG. 5 An example of a diagram C correlating the porosity and the thermal conductivity in the case where secondary electron images from the scanning electron microscope are used.
Figure 6:
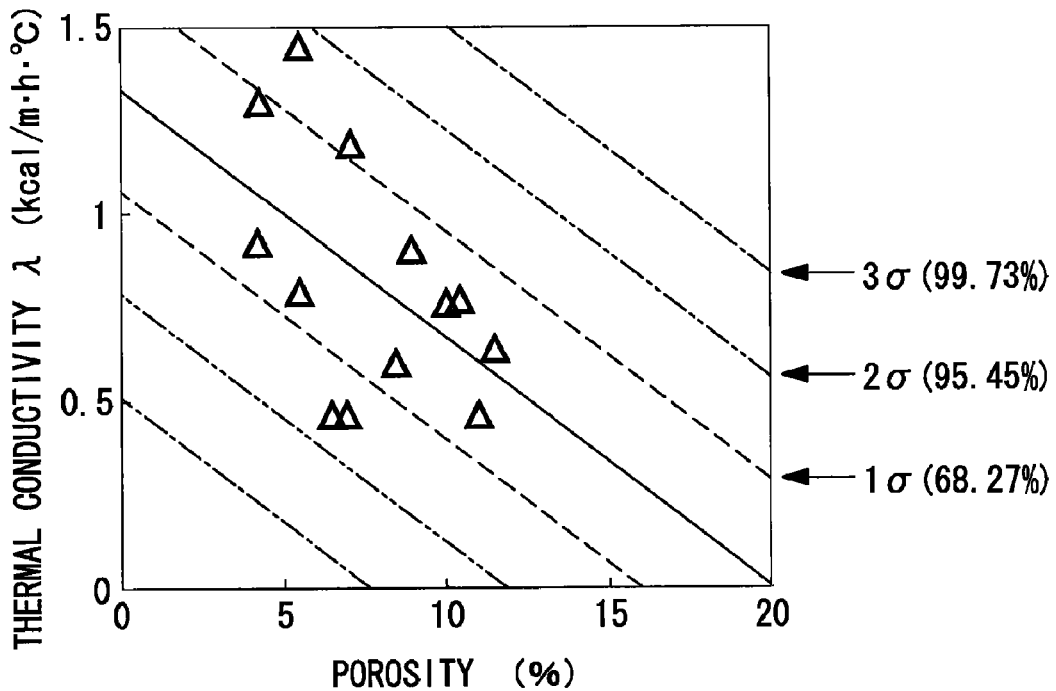
FIG. 6 An example of a diagram C correlating the porosity and the thermal conductivity in the case where an optical microscope is used.

With respect to identical specimens (a total of 13 specimens), pores and stratified formation defects of each specimen were detected based on a backscattered electron image and a secondary electron image from a scanning electron microscope and an optical microscope image. FIG. 4 is a diagram correlating the porosity obtained by detecting the pores and stratified formation defects using the backscattered electron images from the scanning electron microscope and the thermal conductivity. FIG. 5 is a diagram correlating the porosity obtained by detecting the pores and stratified formation defects based on the secondary electron images from the scanning electron microscope and the thermal conductivity. FIG. 6 is a diagram correlating the porosity obtained by detecting the pores and stratified formation defects based on the optical microscope images and the thermal conductivity. In these figures, the horizontal axis is porosity, and the vertical axis is thermal conductivity. The solid diagonal lines drawn in the figures indicate average lines of the measured values. Moreover, the dashed lines, the long-dashed-double-short-dashed lines, and the long-dashed-short-dashed lines in the figures indicate 1σ, 2σ, and 3σ deviation bands, respectively.

Referring to FIG. 6, which was obtained from the optical microscope images, although there is a correlation between the porosity and the thermal conductivity, the deviation bands (1σ, 2σ, and 3σ) are wide, and the measured points vary widely. On the other hand, referring to FIGS. 4 and 5, which were obtained from the scanning electron microscope images, the deviation bands are narrow, and the measured points vary little. The reason for this is that since minute stratified formation defects can be observed under a scanning electron microscope, the physical property acquiring apparatus can detect even a minute stratified formation defect. The use of a scanning electron microscope for structure observation improves the accuracy with which the porosity is calculated, so that the accuracy of the acquired physical property is also improved. In particular, the use of a backscattered electron image can reduce variation of measured points as shown in FIG. 4 and hence is preferable.

In the above-described embodiment, the operator performs the detection of the pores and stratified formation defects, the calculation of the porosity, and the creation of the correlation diagrams; however, the process from the detection of pores and stratified formation defects to the creation of correlation diagrams can be performed by the physical property acquiring apparatus or other apparatuses. In this case, preferably, the time and the operator's effort required for the process from the detection of pores and stratified formation defects to the creation of correlation diagrams can be significantly reduced. In particular, in the case where the physical property acquiring apparatus performs the above-described process, the step of inputting the correlation diagrams to the physical property acquiring apparatus can also be omitted, and accordingly the process can be further simplified.

The physical property acquiring apparatus can further include a remaining lifetime acquiring section. The remaining lifetime acquiring section of the physical property acquiring apparatus uses the Young's modulus and the thermal conductivity acquired by the above-described physical property acquiring section to calculate distortion that occurs in the thermal barrier coating by thermal stress analysis, and acquires the remaining lifetime obtained from the distortion. The operator estimates that the remaining lifetime acquired by the physical property acquiring apparatus is the remaining lifetime of the thermal barrier coating when the turbine has been operated under the above-described operating conditions. Furthermore, the operator estimates that the estimated remaining lifetime of the thermal barrier coating is the remaining lifetime of the high-temperature member of the turbine.

It is to be understood that the method for estimating a physical property of the present invention is not limited to the foregoing embodiments, and any combinations within the scope of the present invention are possible.

The invention claimed is:

1. A method for estimating a physical property of a ceramic, the method comprising:
    a step in which a computer calculates a Larson-Miller parameter from a time for which and a temperature at which the ceramic is heated;
    a step in which the computer acquires a porosity of the ceramic corresponding to the calculated Larson-Miller parameter, based on the calculated Larson-Miller parameter and a diagram correlating the Larson-Miller parameter and the porosity that is determined on the basis of an image obtained using a scanning electron microscope from samples having the same composition as the ceramic, the diagram being stored in a memory of the computer; and
    a step in which the computer acquires the physical property of the ceramic corresponding to the acquired porosity, based on the acquired porosity and a diagram correlating the porosity and the physical property obtained from samples having the same composition as the ceramic, the diagram being stored in a memory of the computer.

2. The method for estimating a physical property of a ceramic according to claim 1, wherein the physical property is Young's modulus.

3. A method for estimating a physical property of a thermal barrier coating, wherein at least one of the Young's modulus and the thermal conductivity of a ceramic layer of the thermal barrier coating formed on a high-temperature member is acquired using the method for estimating a physical property of a ceramic according to claim 2.

4. A method for estimating a remaining lifetime of a thermal barrier coating, wherein the remaining lifetime of the thermal barrier coating is acquired using at least one of the Young's modulus and the thermal conductivity of the ceramic layer acquired by using the method for estimating a physical property of a thermal barrier coating according to claim 3.

5. A method for estimating a remaining lifetime of a high-temperature member, wherein the remaining lifetime of the high-temperature member is estimated from the remaining lifetime of the thermal barrier coating acquired by using the method for estimating a remaining lifetime of a thermal barrier coating according to claim 4.

6. The method for estimating a physical property of a ceramic according to claim 1, wherein the physical property is thermal conductivity.

7. A method for estimating a physical property of a thermal barrier coating, wherein at least one of the Young's modulus and the thermal conductivity of a ceramic layer of the thermal barrier coating formed on a high-temperature member is acquired using the method for estimating a physical property of a ceramic according to claim 6.

8. A method for estimating a remaining lifetime of a thermal barrier coating, wherein the remaining lifetime of the thermal barrier coating is acquired using at least one of the Young's modulus and the thermal conductivity of the ceramic layer acquired by using the method for estimating a physical property of a thermal barrier coating according to claim 7.

9. A method for estimating a remaining lifetime of a high-temperature member, wherein the remaining lifetime of the high-temperature member is estimated from the remaining lifetime of the thermal barrier coating acquired by using the method for estimating a remaining lifetime of a thermal barrier coating according to claim 8.

10. A method for estimating a physical property of a thermal barrier coating, wherein at least one of the Young's modulus and the thermal conductivity of a ceramic layer of the thermal barrier coating formed on a high-temperature member is acquired using the method for estimating a physical property of a ceramic according to claim 1.

11. A method for estimating a remaining lifetime of a thermal barrier coating, wherein the remaining lifetime of the thermal barrier coating is acquired using at least one of the Young's modulus and the thermal conductivity of the ceramic layer acquired by using the method for estimating a physical property of a thermal barrier coating according to claim 10.

12. A method for estimating a remaining lifetime of a high-temperature member, wherein the remaining lifetime of the high-temperature member is estimated from the remaining lifetime of the thermal barrier coating acquired by using the method for estimating a remaining lifetime of a thermal barrier coating according to claim 11.

13. A physical property acquiring apparatus comprising:
   a Larson-Miller parameter calculating section for calculating a Larson-Miller parameter from a time for which and a temperature at which a ceramic is heated;
   a porosity acquiring section for acquiring a porosity of the ceramic corresponding to the calculated Larson-Miller parameter, based on the Larson-Miller parameter calculated by the calculating section and a diagram correlating the Larson-Miller parameter and the porosity that is determined on the basis of an image obtained using a scanning electron microscope from samples having the same composition as the ceramic; and
   a physical property acquiring section for acquiring a physical property of the ceramic corresponding to the acquired porosity, based on the porosity acquired by the porosity acquiring section and a diagram correlating the porosity and the physical property obtained from samples having the same composition as the ceramic.

14. The physical property acquiring apparatus according to claim 13, further comprising a remaining lifetime acquiring section for acquiring a remaining lifetime of a thermal barrier coating using the physical property acquired by the physical property acquiring section.

* * * * *